United States Patent [19]

Geria

[11] Patent Number: 4,702,916
[45] Date of Patent: Oct. 27, 1987

[54] ANALGESIC STICK COMPOSITIONS

[75] Inventor: Navin Geria, Warren, N.J.

[73] Assignee: Warner-Lambert Company, Morris Plains, N.J.

[21] Appl. No.: 804,211

[22] Filed: Dec. 3, 1985

[51] Int. Cl.$^4$ .......................... A61K 9/00; A61K 9/06
[52] U.S. Cl. .............................. 424/400; 424/DIG. 5;
514/692; 514/514; 514/817; 514/848; 514/906; 514/944
[58] Field of Search ................... 424/DIG. 5, 64, 400; 514/692, 514, 848, 906, 944, 817

[56] References Cited

U.S. PATENT DOCUMENTS

| 1,870,107 | 8/1932 | Fuller | 514/692 |
|---|---|---|---|
| 2,857,315 | 10/1958 | Teller | 424/DIG. 5 |
| 3,113,908 | 12/1963 | Pieroh et al. | 514/514 |
| 3,957,969 | 5/1976 | Fujiyama et al. | 424/DIG. 5 |
| 4,039,664 | 8/1977 | Stoughton et al. | 424/DIG. 5 |
| 4,504,465 | 3/1985 | Sampson et al. | 424/DIG. 5 |
| 4,533,546 | 8/1985 | Kishi et al. | 514/944 |
| 4,545,992 | 10/1982 | Kamishita | 514/944 |
| 4,617,185 | 10/1986 | Di Pietro | 424/DIG. 5 |

FOREIGN PATENT DOCUMENTS

| 2077787 | 5/1971 | France | 514/906 |
|---|---|---|---|
| 53-109933 | 9/1978 | Japan | 514/692 |
| 56-53611 | 5/1981 | Japan | 424/DIG. 5 |
| 57-125752 | 8/1982 | Japan | 514/692 |

*Primary Examiner*—Ronald W. Griffin
*Attorney, Agent, or Firm*—Daniel A. Scola, Jr.; Gary M. Nath

[57] ABSTRACT

An analgesic stick composition comprising
(i) a delivery system comprising about 10 to about 65% by weight alcohol; about 6 to about 10% by weight of an alkali metal salt of a saturated fatty acid gelling agent having from about $C_8$ to about $C_{22}$; about 10 to about 30% water; and
(ii) an analgesic compound selected from the group consisting of oleoresin capsicum, capsicum, capsaicin, camphor, allyl isothiocyanate, methyl nicotinate, menthol and mixtures thereof.

8 Claims, No Drawings

ANALGESIC STICK COMPOSITIONS

This invention concerns an analgesic gel stick composition which can be used topically to soothe muscular aches and pains and related disorders. The inventive compositions use as a vehicle an aqueous mixture of an alkali metal salt of a saturated fatty acid ($C_{8-20}$) in combination with alcohol and a compatible analgesic compound. These compositions when applied topically quickly permeate into the stratum corneum, generating warmth and visible reddening of the skin in just a few minutes.

Cosmetic gel stick compositions are well known in the art. Antiperspirants, deodorants, lipsticks and the like all use gel stick technology. Various categories of stick technology exist. For example: suspensoid sticks, which have a finely divided grade of antiperspirant compound dispersed in an emollient vehicle; solution sticks, which contain an alcohol soluble antiperspirant in an alcoholic solution; and compressed sticks, which use isostatic compaction techniques to compress antiperspirant powder and cellulosic binders into solid forms.

Various traditional problems exist in stick technology. For example product deposition must be such that a satisfactory use-up rate and adequate delivery of the active to the skin is obtained. voids often occur within the stick itself due to nonhomogeneous mixing of the ingredients, or variations in pouring temperature. In addition to these problems, considerations as to fabric staining potential of the stick composition, package compatability, friability, syneresis and overall aesthetics must be addressed.

Heretofore, the art has not disclosed an analgesic gel stick composition. The reasons for this are largely due to incompatability of analgesic compounds with conventional gel delivery vehicles. Gel stick formulations are generally either wax-based or soap based (e.g., sodium stearate) systems. When conventional topical analgesic compounds such as methyl salicylate (MS) and triethanolamine salicylate (TES) are incorporated in either of these systems, unacceptable and ineffective products result. Wax-based stick compositions containing, for example, vegetable or mineral waxes tend to trap within the waxy vehicle the analgesic, such that the analgesic does not come into direct contact with the skin and consequently fails to deliver warmth or other effect within an acceptable time period. For example, several hours might elapse before the user feels any effect of the analgesic. The product is therefore unlikely to be acceptable to the consumer in need of more immediate relief. Additionally, the intensity of the analgesic is likely to be diminished, since only a portion of it may come into direct contract with the skin during a specific time period. Without wishing to be bound by any one theory, it is believed that the anhydrous or hydrophobic nature of the wax-based systems is largely responsible for this shortcoming. Hydration of the skin facilitates transport of the analgesic transdermally. The wax-based system fails to hydrate the skin and consequently also fails to transport the analgesic across the epidermis layer. Instead, the wax-based systems cause occulsion of the skin and can preclude effective penetration.

For example, Applicants have determined that a variety of analgesic compounds, e.g., MS, TES, menthol, methyl nicotinate and oleoresin capsicum, when placed in conventional wax-based stick formulations failed to deliver a perceptable warmth, reddening of the skin or other analgesic effect, even after an hour subsequent to deposition. Attempts to modify the anhydrous nature of the vehicle through the addition of water and/or surfactants showed no detectable change in effectiveness of delivery. The addition of water tended to result in the formation of water beads due to emulsification. The water was therefore unable to impart to the stick as a whole sufficient hydrous character to overcome the preponderance of the wax. No improvement in the stick's ability to hydrate the skin upon application was observed, and thus inadequate analgesic delivery resulted. Additionally, the incorporation of too much water and surfactant tended to have a deterterious effect on the structural integrity of the stick resulting in an unacceptably soft product. Higher amounts of the analgesic compound, within reasonable formulation restrictions, e.g., up to about 15% by weight, also failed to achieve effective delivery of the active to the skin. Moreover, undesirable discoloration at temperatures of 37° C. or more is common with wax-based systems.

It has been discovered that sodium stearate/propylene glycol based stick compositions containing MS as the analgesic are highly unstable due to the chemical incompatability between MS and the vehicle. Methyl salicylate gradually destroys the structural integrity of the stick, making it unacceptably soft and difficult to use. The rigidity of the stick is compromised and syneresis results.

As a result of these problems, gel sticks containing analgesics are not currently marketed. Analgesics have therefore been limited to cremes, lotions, ointments and the like, which are less desirable from a consumer convenience point of view than gel sticks. Additionally, these product forms when applied to the skin leave a wet, sticky or greasy feeling and are inconvenient to use when concerned about soiling of clothing or ease of application.

It is apparent that there is a need for a stable gel stick composition which can effectively deliver a sufficient amount of analgesic topically to produce warmth and soothing effects to the skin as well as the underlying muscle and joint areas within a few minutes time.

The inventive compositions address this need by providing an analgesic gel stick having four essential components. The composition comprises:
(i) a delivery system comprising about 10 to about 65% by weight alcohol; about 6 to about 10% by weight of an alkali metal salt of a saturated fatty acid gelling agent having from about $C_8$ to about $C_{22}$; about 10 to about 30% water;
(ii) and an analgesic compound selected from the group consisting of capsaicin, capsicum, oleoresin capsicum, methyl nicotinate, menthol, camphor, allyl isothiocyanate, and mixtures thereof. Weight percents are based on the total composition.

Those alcohols useful in the delivery system may be selected from a variety of monohydric or polyhydric alcohols and mixtures thereof. The use of monohydric alcohols, such as ethanol or propanol alone, however, is not desirable since these alcohols quickly evaporate, leading to shrinkage of the stick. If a mixture is used, it is therefore preferably to have the mixture be predominately polyhydric alcohol. The ratio of poly- to monohydric alcohol is generally about 3:1 to about 2:1. The use of the monohydric alcohols are efficacious in achieving a cooling effect on the skin. It is most preferred however that a polyhydric alcohol be used alone.

Alcohols which are useful include those having the formula $C_nH_{2n+1}OH$ wherein $n = 1$ to 6. Generally, it is preferred that the alcohol be aliphatic and contain from 2 to 6 carbon atoms and from 1 to 3 hydroxyl groups. Ethanol. propanol, isopropanol, methanol, propylene glycol, sorbitol, polyethylene glycol, glycerol, carbitol, tri-methylene glycol, 1,3-butane-diol, 1,4-butane-diol, and mixtures thereof are typically used. The most preferred alcohol is propylene glycol.

The alcohols are present in amounts of about 10 to about 65% by weight of the total stick composition and preferably about 10 to about 20% by weight. The alcohol is believed to complex with the gelling agents once the stick composition begins to solidify during processing. Thus, initially the alcohol serves as a solvent or carrier for the gelling agent and subsequently, via hydrogen bonding, aids in the formation of the gel structure of the stick. The alcohol acts to some degree as a plasticizer to prevent the final stick product from becoming brittle once it is completely solidified. Additionally, the alcohol component aids in preventing the film which is deposited on the skin during use from drying too rapidly. Finally, the alcohol also prevents the deposition on the skin of a powdery film of the acid-soap component (e.g., sodium stearate).

Those gelling agents useful include the alkali metal stearate and palmitates. These materials are often referred to in the art as alkali metal soaps or acid-soaps. For example, sodium stearate, potassium stearate, sodium palmitate, potassium palmitate, sodium potassium stearate, among others, are particularly beneficial. Sodium stearate is the most preferred gelling agent. The term "sodium stearate" is herein used to connote the sodium salt of a mixture of fatty acids, of which stearic acid and palmitic acid predominate and with relatively small proportions of closely related fatty acids. While these agents may be prepared separately and then added to the alcohol component, it is preferred that the entire vehicle be made simultaneously and that the gelling agent be formed in situ during this process. To do so, aqueous alkali such as sodium or potassium hydroxide are added to a warm aqueous/alcohol solution of the fatty acid, e.g., stearic or palmitic acid. For example, aqueous sodium hydroxide is added to propylene glycol or ethyl alcohol solution and mixed at about 70° to about 75° C. until a clear solution results. The solution is allowed to cool to about 45° to about 50° C., at which time the analgesic is added in liquid form. The composition is then poured into the desired mold and further cooled until it solidifies. The resultant stick is rigid and possesses neither syneresis nor shrinkage problems. The inventive sticks are stable and exhibit no separation of ingredients.

Those analgesic compounds useful in the invention are limited to those which are compatible with the fatty acid gel vehicle. Thus, as previously discussed, methyl salicylate is not useful as the primary active in the instant compositions. It can be incorporated merely for its medicinal odor, however, since this odor is well identified by consumers with analgesic products. Menthol, oleoresin capsicum, capsicum, capsaicin, camphor, allyl isothiocyanate and methyl nicotinate are the useful analgesics. Mixtures of these are useful. These actives are both compatible with the vehicle and as well as being capable of delivering perceptable warmth to the skin and underlying tissues, muscles and joints. While an effective therapeutic amount is desired, generally these actives are present in amounts of about 0.25 to about 15% by weight and preferably about 1 to about 8% by weight of the total composition.

The inventive compositions generate perceptable warmth and visible reddening of the skin within about five minutes or topical application.

The relative proportions between quantities of fatty acid gelling agent, propylene glycol alcohol and water are optimized so as to provide a final stick product having firmness and warming effect within relatively wide ranges of personal preference.

A number of additional additives are useful in the inventive compositions. Emollients, emulsifiers, surfactants, coloring agents, dyes, fillers, ultraviolet absorbers, bacteriostats, gelling agents, fragrances, preservatives, humectants, chelating agents, waxes and mixtures thereof may be useful.

Among these additional additives are those ingredients which are typically categorized as emollients or emulsifiers. These ingredients serve to aid in deposition of the composition onto the skin, as well as to remove any undesired residue from the skin after use. Suitable emollients would include fatty acid esters such as cetyl palmitate, diisopropyl adipate, isopropyl isostearate, isostearyl isostearate, lauryl lactate, polyalkylene glycols and mixtures thereof. Additional liquid emollients suitable for use include those described by Balsam & Sagarin, *Cosmetics Science & Technology*, 2nd Ed., Vol. 1, Wiley-Interscience, 1972, Chapter 2, pp 27–104. Certain of these agents may be utilized to improve the lubricity of the composition, including silicone oils or fluids such as substituted and unsubstituted polysiloxanes; for example, a polysiloxane such as dimethyl polysiloxane, also known as dimethicone, as well as cyclomethicones, may be utilized for this purpose. These ingredients may be present in amounts conventionally used in the gel-stick industry.

A variety of materials may be utilized as emulsifiers, including high molecular weight polyethylene glycols, fatty alcohols such as stearyl alcohol, myristyl alcohol and the like. Numerous surfactants may also be employed. These would include, without limitation, the non-ionic surfactants such as the poly-alkanolamines, e.g., triethanolamine, polyethylene glycol stearate, polyethylene glycol laurate, poly-oxyethylene and polyoxypropylene compounds (e.g., as derivatives of sorbitan and fatty alcohol ethers and esters, polyoxypropylene polyoxyethylene condensate), fatty acid esters of polyhydric alcohols and amine oxides; anionic surfactants, such as alkyl carboxylates, acyl lactylates, sulfuric acid esters (e.g., sodium lauryl sulfate), ester-linked sulfonates, and phosphated ethoxylated alcohols. Emulsifiers and/or surfactants may be employed in amounts of about 0.25 to about 5% by weight of the total composition.

Suitable humectants include glycerin, propylene glycol, polyethylene glycol and mixtuers thereof. Preferably, glycerin or sorbitol are used. They are generally present in amounts of about 0.5 to about 3% by weight of the total composition.

Pigments and coloring agents include titanium dioxide, FD & C dyes and other well-known and conventional ingredients.

A variety of bacteristats or preservatives may be incorporated providing they are compatible with the acid-soap gelling agent. Substituted phenols and derivatives thereof are one such class of preservatives which may be added. Examples include the chloro-substituted phenoxy phenols, such as 5-chloro-2-(2,4-dichlorophenoxy)phenol; 3,4,4-trichlorocarbanilide and bithionol, hexachlorophene, triclosan, dichlorophene, among others; Mercury derivatives, such as phenylmercuric acetate; Quaternaries, such as benzethonium chloride, benzalkonium chlorides and cetyl trimethyl ammonium bromide; acids, such as sorbic acid, and a variety of other preservatives such as Kathon CG, a trademark of Rohm & Hass Co. which comprises a mixture of 5-chloro-2-methyl-4-isothiazolin-3-one and 2-methyl-4-isothiazolin-3-one.

With respect to 5-chloro-2-(2,4-dichlorophenoxy)-phenol, this material is commerically available under the trademark IRGASAN® DP 300, available from Geigy Industrial Chemicals Division of Ciba-Geigy Corporation. This compound is well known as a broad-spectrum antimicrobial agent that is useful in the manufacture of a variety of cosmetics, laundry products and the like.

The product set forth in the following examples will harden upon cooling slightly below the pouring temperature due to solidification of the acid-soap gel base. The finished product is stable and needs only to be packaged in a fashion which prevents evaporation of the alcohol and water.

All ingredients of the inventive compositions may be heated together with agitation in a closed vessel fitted with a reflux condenser until clear in appearance. The mixture is then poured at 65° to 70° C. into cylindrical, stick-shaped containers. The order of addition of ingredients may be varied without apparent effect on the final product.

The present invention will be better understood from a consideration of the following illustrative examples, in which all percentages of ingredients are expressed in percent by weight of the total composition unless otherwise indicated.

EXAMPLES

Table I below sets forth four inventive gel stick compositions containing analgesic additives. These compositions employ propylene glycol as the alcohol component, sodium stearate as the gelling agent and a combination of analgesic actives, namely oleoresin capsicum, methyl salicyate (MS), methyl nicotinate and menthol. Triclosan is used as preservative. Although compositions 3 and 4 contain about 0.2% MS, its presence was as levels which are too low for analgesic efficacy. As previously explained, MS is not compatible with the instant gel-stick compositions when used at the levels necessary to produce analgesic effects. Rather, these low levels were intended to give the use the medicated perceptive fragrance known to the commercially available products.

These compositions were prepared by dissolving powdered sodium stearate in a mixture of propylene glycol and water by heating at 70° to 75° C. The resultant solution is clear. The solution is slowly cooled to about 45°–50° C. at which time the analgesics were added, as well as the remainder of the ingredients. The solution was then poured into containers and allowed to further cool. The compositions formed a ridged stick. The stick can be transparent or translucent depending on the particular coloring agents used. No syneresis, shrinkage or separation out of ingredients occurred either immediately upon cooling or after extended shelf life, e.g., after more than one year.

Table II sets forth three comparative prior art gel stick compositions using wax-based systems.

TABLE I (Sodium Stearate - Propylene Glycol - Water Based)

| Ingredient | Inventive Compositions | | | |
|---|---|---|---|---|
| | 1 | 2 | 3 | 4 |
| 1. Propylene Glycol | 60.00 | 50.00 | 50.00 | 50.00 |
| 2. Oleoresin Capsicum bleached 250,000* | 1.00 | 1.00 | 0.25 | 0.25 |
| 3. Sodium Stearate | 8.00 | 8.00 | 16.00 | 16.00 |
| 4. Methyl Nicotinate* | 1.00 | 1.00 | 1.00 | 1.00 |
| 5. Menthol* | 5.00 | 5.00 | 5.00 | 5.00 |
| 6. D&C Red #30 | 1.00 | 1.00 | 1.00 | 1.00 |
| 7. Triclosan | 0.20 | 0.20 | 0.20 | 0.20 |
| 8. Purified Water | 23.80 | 23.80 | 16.35 | 16.35 |
| 9. Lauryl Lactate** | — | 10.00 | 10.00 | 10.00 |
| 10. Methyl Salicylate*** | — | — | 0.20 | 0.20 |
| | 100.00 | 100.00 | 100.00 | 100.00 |

*Analgesic
**Ceraphyl 41 made by Van Dyke Company, Belleville, N.J.
***Used to give medicated fragrance perception - not for analgesic effect

TABLE II (Methyl Salicyate - Lipophillic Emollients - Wax Based)

| Ingredient | Comparative Prior Art | | |
|---|---|---|---|
| | 5 | 6 | 7 |
| 1. Methyl Salicylate* | 15.00 | 15.00 | 25.00 |
| 2. Witcomide 70** | 27.00 | 27.00 | 27.00 |
| 3. Paraffin Wax | 8.00 | 8.00 | 8.00 |
| 4. Lauryl Lactate*** | 48.00 | 45.00 | 3.00 |
| 5. Fragrance Fl. M4506 | 2.00 | — | — |
| 6. Purified Water | — | 5.00 | 30.00 |
| 7. Oleoresin Capsicum | — | — | 1.00 |
| 8. Methyl Nicotinate | — | — | 1.00 |
| 9. Menthol | — | — | 5.00 |
| | 100.00 | 100.00 | 100.00 |

*Analgesic
**Polyamide wax
***Ceraphyl 41 made by Van Dyke Company, Belleville, N.J.

PANEL EVALUATION FOR WARMTH PERCEPTION

Compositions 1 through 4 of Table 1 were each individually tested on six panelists for evaluation. The sticks were rubbed on the forearms in a circular manner six times delivering approximately 350–500 mg. of the product onto the skin. Manual massaging was kept to a minimum because most subjects felt that a sufficient film of the product was uniformly deposited on the skin. In less than five minutes, all the panelists reported visible reddening of the applied area and overwhelming feeling of warmth. The sticks of each composition were also rated satisfactory for their organoleptic and aesthetic attributes as well.

Prior art compositions 5, 6 and 7 of Table II were sequentially evaluated by the panelists in the above described manner. Even after waiting for as long as two hours, no perception of warmth was felt by any of the panelists.

It is apparent that the inventive compositions are unique in their ability to deliver effective amounts of analgesic in a composition which remains stable in stick form. This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

We claim:

1. An analgesic stick composition comprising (i) a delivery system comprising about 10 to about 65% by weight alcohol; about 6 to about 10% by weight of an alkali metal salt of a saturated fatty acid gelling agent having from about $C_8$ to about $C_{22}$; about 10 to about 30% water; and (ii) an analgesic compound selected from the group consisting of oleoresin capsicum, capsicum, camphor, capsaicin, allyl isothiocyanate, methyl nicotinate, menthol and mixtures thereof.

2. The composition of claim 1 wherein the alcohol is a polyhydric alcohol selected from the group consisting of propylene glycol, polyethylene glycol, carbitol, trimethylene glycol, 1,3-butanediol, 1,4-butane-diol, sorbitol, glycerol and mixtures thereof.

3. The composition of claim 1 wherein the alcohol is a monohydric alcohol of a lower alkyl.

4. The composition of claim 1 wherein the gelling agent is selected from the group consisting of sodium stearate, potassium stearate, sodium palmitate, potassium palmitate and mixtures thereof.

5. The composition of claims 1, 2 or 4 wherein additional additives are incorporated selected from the group consisting of emulsifiers, emollients, surfactants, coloring agents, fillers, ultraviolet absorbers, bacteriostats, other gelling agents, fragrances, preservatives, humectants, chelating agents, waxes, dyes and mixtures thereof.

6. The composition of claim 5 wherein the emulsifiers are polyoxyethylene fatty ethers, polyoxyethylene sorbitan fatty esters, fatty amides, polyoxypropylene polyoxyethylene condensate and mixtures thereof.

7. The composition of claim 5 wherein the emollient is selected from the group comprising of cyclomethicones, polyaklylene glycol, lauryl lactate, cetyl palmitate, diisopropyl adipate, isopropyl isostearate, isostearyl isostearate and mixtures thereof.

8. The composition of claim 5 wherein the preservatives are triclosan, dichlorophene, hexachlorophene, 5-chloro-2-(2,4-dichlorophenoxy)phenyl, phenylmercuric acetate, benzethonium clhloride, benzalkonium chloride, cetyl trimethyl ammonium chloride and sorbic acid.

* * * * *